(12) United States Patent
Williams et al.

(10) Patent No.: US 6,890,747 B2
(45) Date of Patent: May 10, 2005

(54) PHOSPHOINOSITIDE 3-KINASES

(75) Inventors: Roger Williams, Cambridge (GB); Christian Ried, Berlin (DE); Edward H. Walker, Chesterton (GB); Len Stephens, Horseheath (GB)

(73) Assignees: Warner-Lambert Company, Morris Plains, CA (US); Onyx Pharmaceuticals, Inc., Richmond, CA (US)

( * ) Notice: Subject to any disclaimer, the term of this patent is extended or adjusted under 35 U.S.C. 154(b) by 110 days.

(21) Appl. No.: 09/974,573

(22) Filed: Oct. 9, 2001

(65) Prior Publication Data

US 2003/0022344 A1 Jan. 30, 2003

Related U.S. Application Data

(60) Provisional application No. 60/242,801, filed on Oct. 23, 2000.

(51) Int. Cl.[7] .................................................. C12N 9/12
(52) U.S. Cl. ....................................................... 435/194
(58) Field of Search .......................................... 435/194

(56) References Cited

PUBLICATIONS

Stephens et al The G beta gamma sensitivity of a PI3K is dependent upon a tightly associated adaptor, p101. Cell. Apr. 4, 1997;89(1):105–14.*

* cited by examiner

*Primary Examiner*—Rebecca E. Prouty
*Assistant Examiner*—Sheridan L. Swope
(74) *Attorney, Agent, or Firm*—Gregory Giotta

(57) ABSTRACT

The present invention relates PI3K crystals, polypeptide muteins, polypeptide fragments, antibodies thereto, nucleic acids coding for these polypeptides, methods of modifying PI3Kγ activity, and methods of modulating PI3Kγ activity. These include polypeptides and methods thereof, relating to, e.g., phospholipid binding, lipid kinase activity, modulating Ras activity in activating the PI3Kγ, binding of PI3Kγ to cell membranes, and modulating protein—protein interactions with PI3Kγ.

1 Claim, 8 Drawing Sheets

```
MELENYEQPV VLREDNRRRR RRMKPRSTAA SLSSMELIPI EFVLPTSQRN TKTPETALLH
VAGHGNVEQM KAQVWLRALE TSVSADFYHR LGPDHFLLLY QKKGQWYEIY DKYQVVQTLD
CLRYWKVLHR SPGQIHVVQR HAPSEETLAF QRQLNALIGY DVTDVSNVHD DELEFTRRRL
VTPRMAEVAG RDPKLYAMHP WVTSKPLPEY LLKKITNNCV FIVIHRSTTS QTIKVSADDT
PGTILQSFFT KMAKKKSLMD IPESQNERDF VLRVCGRDEY LVGETPIKNF QWVRQCLKNG
EEIHLVLDTP PDPALDEVRK EEWPLVDDCT GVTGYHEQLT IHGKDHESVF TVSLWDCDRK
FRVKIRGIDI PVLPRTADLT VFVEANIQYG QQVLCQRRTS PKPFTEEVLW NVWLEFSIKI
KDLPKGALLN LQIYCGKAPA LSGKTSAEMP SPESKGKAQL LYYVNLLLID HRFLLRHGEY
VLHMWQLSGK GEDQGSFNAD KLTSATNPDK ENSMSISILL DNYCHPIALP KHRPTPDPEG
DRVRAEMPNQ LRKQLEAIIA TDPLNPLTAE DKELLWHFRY ESLKDPKAYP KLFSSVKWGQ
QEIVAKTYQL LAKREVWDQS ALDVGLTMQL LDCNFSDENV RAIAVQKLES LEDDDVLHYL
LQLVQAVKFE PYHDSALARF LLKRGLRNKR IGHFLFWFLR SEIAQSRHYQ QRFAVILEAY
LRGCGTAMLH DFTQQVQVID MLQKVTIDIK SLSAEKYDVS SQVISQLKQK LENLQNLNLP
QSFRVPYDPG LKAGALVIEK CKVMASKKKP LWLEFKCADP TALSNETIGI IFKHGDDLRQ
DMLILQILRI MESIWETESL DLCLLPYGCI STGDKIGMIE IVKDATTIAK IQQSTVGNTG
AFKDEVLSHW LKEKCPIEEK FQAAVERFVY SCAGYCVATF VLGIGDRHND NIMISETGNL
FHIDFGHILG NYKSFLGINK ERVPFVLTPD FLFVMGTSGK KTSLHFQKFQ DVCVKAYLAL
RHHTNLLIIL FSMMLMTGMP QLTSKEDIEY IRDALTVGKS EEDAKKYFLD QIEVCRDKGW
TVQFNWFLHL VLGIKQGEKH SA
```

Fig. 8

PHOSPHOINOSITIDE 3-KINASES

This Application claims priority from U.S. Provisional Application No. 60/242,801, filed Oct. 23, 2000.

BACKGROUND OF THE INVENTION

Phosphoinositide 3-kinases (PI3Ks) are ubiquitous lipid kinases playing key roles both as signal transducers downstream of cell-surface receptors and in constitutive intracellular membrane and protein trafficking pathways. All PI3Ks are dual specificity enzymes with a lipid kinase activity capable of phosphorylating phosphoinositides at the 3-hydroxyl and with a protein kinase activity. The products of PI3K-catalysed reactions, phosphatidylinositol 3,4,5-trisphosphate (PtdIns(3,4,5)$P_3$), PtdIns(3,4)$P_2$ and PtdIns(3)P act as second messengers for a variety of signal transduction pathways, including those essential to cell proliferation, adhesion, survival, cytoskeletal rearrangement and vesicle trafficking (1,2).

The mammalian PI3Ks can be divided into three classes based on their structure and substrate specificity (2). The class I PI3Ks are receptor-regulated heterodimeric enzymes that preferentially phosphorylate PtdIns(4,5)$P_2$ in vivo. The class IA PI3Ks (consisting of p110α, p110β, or p110δ catalytic subunits) associate with an 85 kDa adaptor that is essential for interaction of these PI3Ks with receptor tyrosine kinases. The class IB PI3K (PI3Kγ) is activated by heterotrimeric G protein subunits and associates with a p101 adaptor that is important for full responsiveness to Gβγ heterodimers (3,4). Class I PI3Ks are also activated by Ras. Class II PI3 Ks are distinguished by a C-terminal C2 domain and preferentially use PtdIns and PtdIns(4)P as substrates. Class III enzymes phosphorylate only PtdIns and lack the Ras-binding domain.

BRIEF DESCRIPTION OF THE DRAWING

FIG. 8 shows the complete amino acid sequence of porcine PI3Kγ.

DESCRIPTION OF THE INVENTION

Figure 1:
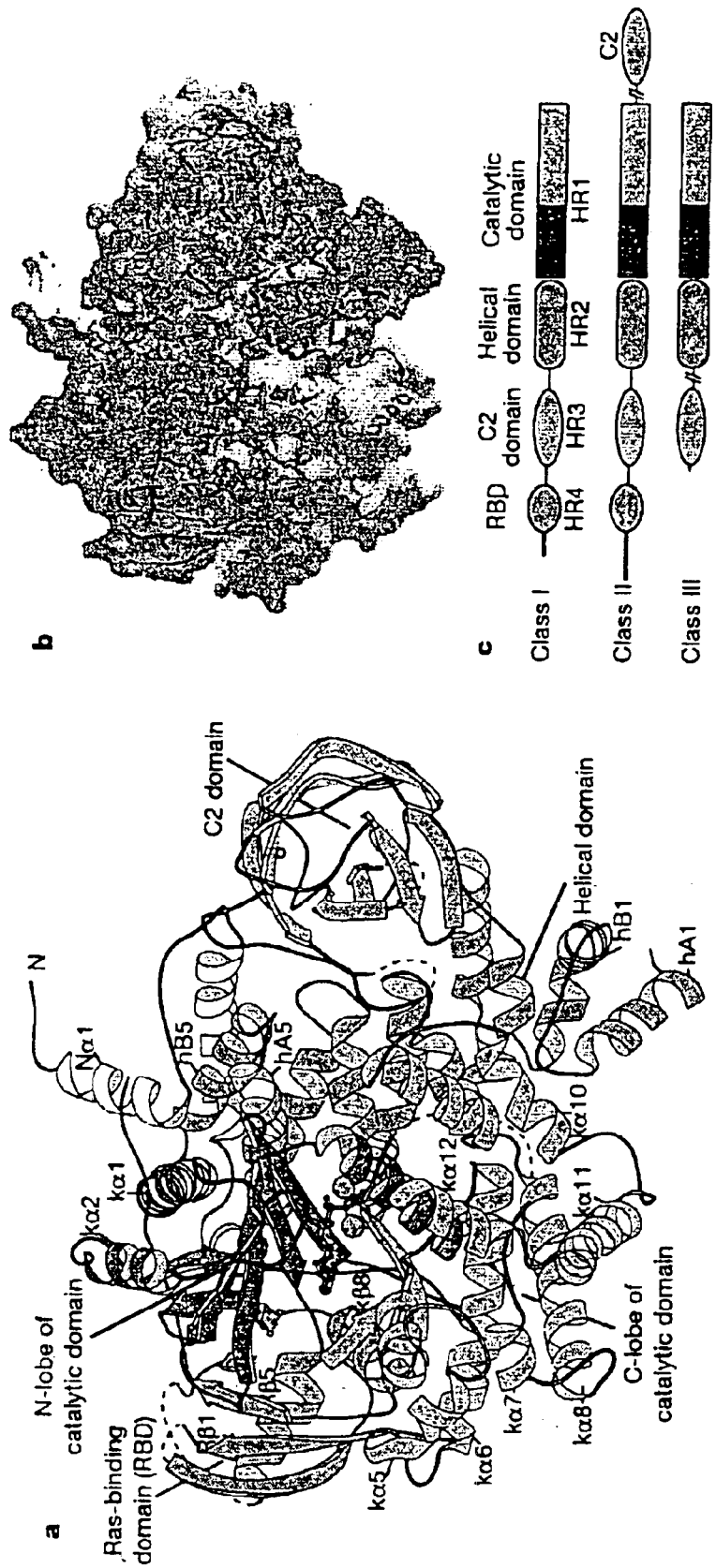
FIG. 1 shows the overall structure of PI3Kγ (A) A ribbon diagram of PI3K (prepared with MOLSCRIPT) showing the four domains: the RBD, the C2 domain, the helical domain and the catalytic domain with N-lobe and C-lobe. The N-terminal region preceding the RBD and the ordered portion between the RBD and C2 domain are white. (B) The solvent-accessible surface of the enzyme in the same orientation (prepared with GRASP (29)). (C) A block diagram showing the domain organization of the PI3K classes.

The present invention relates to phosphoinositide 3-kinases (PI3Ks), a class of enzymes involved in signal transduction and in constitutive intracellular membrane protein trafficking pathways. PI3Ks possess dual catalytic functions, possessing both lipid kinase and protein kinase activity. The products of PI3K-catalyzed reactions are second messengers in a variety of signal transduction pathways, including those involved in cell proliferation, adhesion, survival, cytoskeletal rearrangement, and vesicle trafficking. Thus, modulating its activities is useful for regulating cellular activities, e.g., involved in inflammation, repair, healing, development, and differentiation (e.g., for regulating stem cell growth and differentiation).

In accordance with the present invention, the three dimensional structure of a PI3Kγ has been determined. The present invention thus relates to a PI3Kγ crystal with unit dimensions of about a=143.3 Å, b=67.6 Å, c=107.0 Å, and β=95.9°. The crystals have C2 symmetry and contain one molecule in the unit cell. Crystals can be grown and analyzed by any effective methods, such as methods described in the examples below.

The present invention also relates to PI3Kγ polypeptide muteins, polypeptide fragments, antibodies thereto, nucleic acids coding for these polypeptides, methods of modifying PI3Kγ activity, and methods of modulating PI3Kγ activity. These include polypeptides and methods thereof, relating to, e.g., phospholipid binding, lipid kinase activity, modulating Ras activity in activating the PI3Kγ, binding of PI3Kγ to cell membranes, and modulating protein—protein interactions with PI3Kγ. Polypeptides, nucleic acids, and antibodies can be prepared according to any effective method.

By the term "mutein," it is meant any non-naturally occurring mutation. Mutations can be introduced by any suitable method, e.g. by site-directed mutagenesis, by routinely by modifying or mutating a nucleotide sequence coding for an amino acid sequence of FIG. 3, and selecting for those mutations that affect one or more of its activities, e.g., by measuring activity as described in Bondeva et al.,

*Science,* 282:293–296, 1998. Muteins can comprise amino acid substitutions, insertions, and deletions, including replacing naturally-occurring amino acids with non-naturally occurring amino acids. Amino acid substitution can be made by replacing one homologous amino acid for another. Homologous amino acids can be defined based on the size of the side chain and degree of polarization, including, small nonpolar: cysteine, proline, alanine, threonine; small polar: serine, glycine, aspartate, asparagine; large polar: glutamate, glutamine, lysine, arginine; intermediate polarity: tyrosine, histidine, tryptophan; large nonpolar: phenylalanine, methionine, leucine, isoleucine, valine. Homologous acids can also be grouped as follows: uncharged polar R groups, glycine, serine, threonine, cysteine, tyrosine, asparagine, glutamine; acidic amino acids (negatively charged), aspartic acid and glutamic acid; basic amino acids (positively charged), lysine, arginine, histidine. Homologous amino acids also include those described by Dayhoff in the Atlas of Protein Sequence and Structure 5, 1978, and by Argos in EMBO J., 8, 779–785, 1989. Homologous amino acid replacement or modification can be utilized when it is desired to maintain, or enhance a PI3Kγ activity. Non-homologous amino acid replacement or modification can be utilized when it is desired to destroy or decrease a PI3Kγ activity. A polypeptide mutein, and its corresponding nucleotide coding sequence, can have an amino acid sequence as set forth in FIG. 3 except where one or more positions are substituted by homologous amino acids, e.g., where there are 1, 5, 10, 15, or 20 substitutions. Amino acid substitutions can also be made based on analogy to related other PI3Ks.

A PI3Kγ of the present invention, fragments, and muteins thereof, can also comprise various modifications, where such modifications include lipid modification, methylation, phosphorylation, glycosylation, covalent modifications (e.g., of a side chain of an amino acid). Modifications to the polypeptide can be accomplished according to various methods, including recombinant, synthetic, chemical, etc.

The present invention also relates to antibodies which are "specific-for" a particular polypeptide comprising a defined amino acid sequence of a PI3Kγ. The phrase "specific-for" indicates that the antibody is selective for the defined amino acid sequence. The amino acids sequences can possess other immunogenic activities, as well, e.g., stimulating of T-cells, macrophages, B-cells, dendritic cells, etc. These responses can be measured routinely.

An aspect of the present invention relates to polypeptides, fragments and muteins, of PI3Ks that possess phospholipid binding, and PI3Ks which display modified phospholipid binding activity. As mentioned, PI3Ks phosphorylate phosphoinositides, and analogs and derivatives thereof, at a 3-hydroxyl group. The catalytic reaction involves binding of a phospholipid substrate to the enzyme. A polypeptide fragment of PI3Kγ has been identified which possesses phospholipid activity. This fragment can also be referred to a phospholipid binding domain to indicate its primary activity. By the term "fragment," it is meant any sequence of amino acids which is less than the full-length size of a PI3K. A PI3K phospholipid binding domain, preferably consists essentially of a C-terminal helix kα12, catalytic loop, activation loop, and amino acid residues Lys807, Lys808, Arg947, and Lys973. The catalytic loop preferably consists essentially of amino acids 943–951 and the activation loop preferably consists essentially of amino acids 964–988, and kα12 preferably consists essentially of amino acids 1081–1090.

A PI3K mutein, or polypeptide fragment thereof, which possesses phospholipid binding activity preferably comprises Lys807, Lys808, Arg947, and Lys973. Muteins which possess less than normal phospholipid binding activity preferably comprise amino acid substitutions at one or more positions Lys807, Lys808, Arg947, and Lys973. Phospholipid binding to PI3K can be measured conventionally, e.g., using radiolabeled phospholipids.

By the phrase "less than normal binding activity," it is meant that such mutein (full-length PI3K or a fragment thereof), displays an amount of activity which is reduced when compared to the wild-type, not mutated, enzyme. Such amount can be reduced by any quantity, e.g., 5%, 10%, 25%, 50%, or even a total loss of activity. Phospholipid binding activity can be measured by any effective method.

Figure 3:
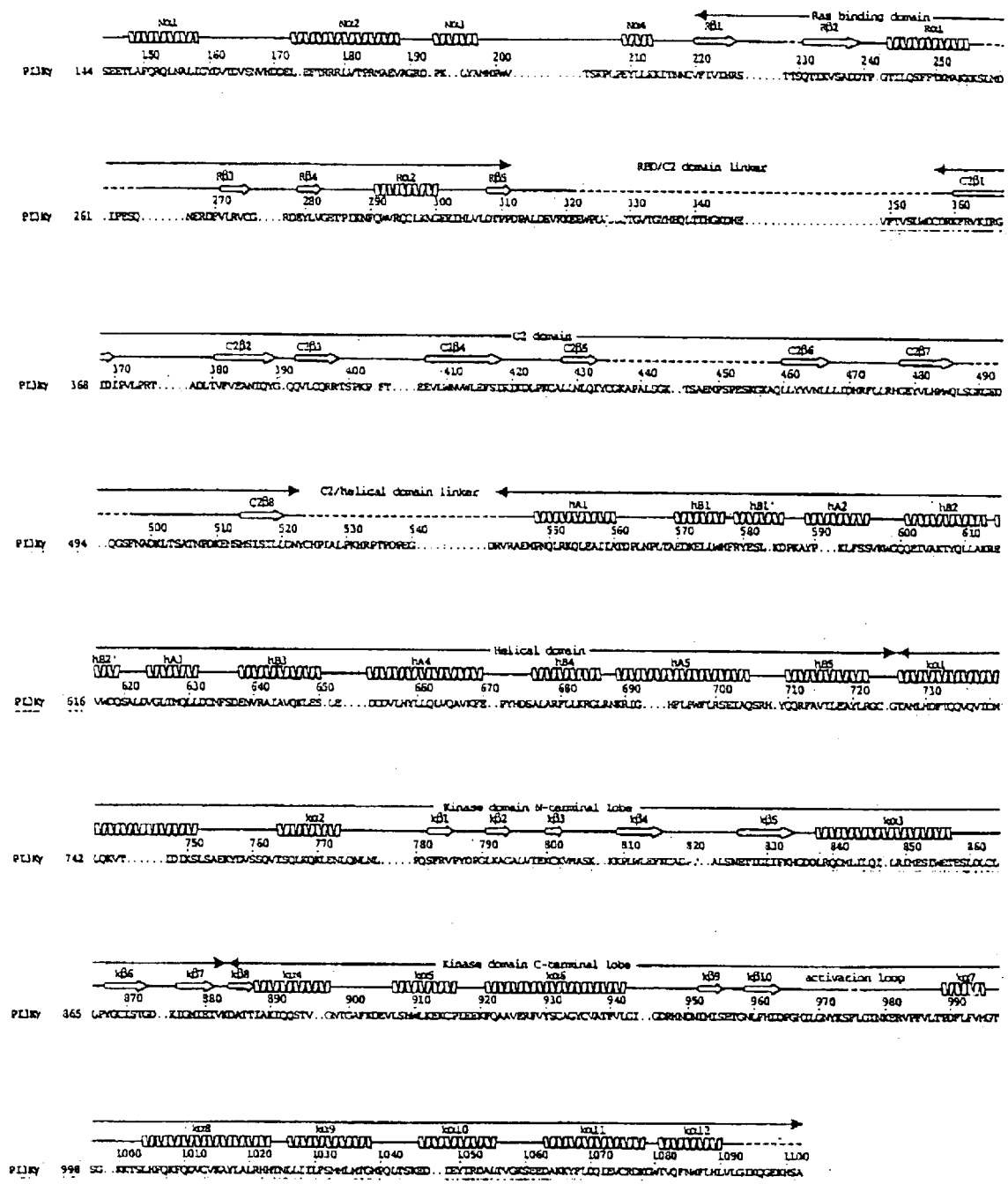
FIG. 3 show the complete amino acid sequence of a porcine PI3Kγ. The ( . . . ) indicate gaps when the PI3Kγ is aligned with other members of the PI3K family. The other PI3Ks are not shown, but are incorporated by reference to Walker et al., Nature, 402:313–320, 2000.

An isolated polypeptide mutein of PI3K can comprise a phospholipid binding domain, which domain comprises the C-terminal helix kα12, catalytic loop, and activation loop sequences of FIG. 3, and at least 95% sequence identity to the remaining sequence in FIG. 3. In general, the phrase that a domain, region, etc., comprises a sequence of FIG. 3, it meant that the polypeptide has 100% sequence identity to the sequence disclosed in FIG. 3. For this mutein, the phospholipid domain has 100% sequence identity to its sequence in FIG. 3, but the remaining regions have less 100% sequence identity, such as 70%, 75%, 80%, 85%, 90%, 95%, 99%, or more, but less than 100%. Such muteins can lack all known catalytic activities of PI3K, but still possess the phospholipid binding activity.

The present invention also relates to methods of modulating phospholipid binding activity, e.g., binding of a phospholipid substrate to a PI3K enzyme, fragment, mutein, etc. Modulating can be accomplished in any manner, e.g., modifying the amino acid sequence of PI3K, contacting an active site or region with a modifying agent, e.g., a chemical agent which modifies the chemical groups, contacting an active site or region with a ligand, e.g., an antibody. In particular, as mentioned above, regions involved in phospholipid binding, comprise a C-terminal helix kα12, catalytic loop, and activation loop. The catalytic loop preferably consists essentially of amino acids 943–951 and the activation loop preferably consists essentially of amino acids 964–988. Modification of these regions, particularly amino acids Lys807, Lys808, Arg947, and Lys973, can affect substrate binding activity.

Another aspect of the present invention relates methods of modulating lipid kinase catalysis. Inhibition can be accomplished by various methods, including, e.g., modifying the amino acid sequence of a PI3K, contacting an active site, or amino acid residue thereof, with a modifying agent, etc. For example, the histidine at amino acid 968 has been identified as involved in the deprotonation of the 3-hydroxy of the lipid headgroup. Alteration of the histidine would be expected to effect the enzyme's activity, e.g., by inhibiting, blocking, decreasing, reducing, enhancing, increasing, etc., its activity. Non-conservative (non-homologous) amino acid substitution can be expected to reduce catalytic activity. Conservative (homologous) amino acid substitution can be expected to not affect, or to increase catalytic activity.

Another way of modulating the lipid kinase activity is to modify the amino acid sequence of a produced PI3K, e.g., at its active site, such as the amino acid residues surrounding and including His968. Any agent which can chemically modify an amino acid can be used, including, oxidizing agents, reducing agents, alkylating agents, etc. In addition, ligands which attach to the active site can be used, such as substrate analogs, antibodies, e.g., an antibody which recognizes an amino acid sequence comprising His968.

The present invention relates to polypeptides, muteins, etc., which comprise His968. Such polypeptide fragments can be useful to prepare antibodies, to inhibit lipid kinase activity by competing for substrates, etc. Useful polypeptides include, e.g., polypeptides which consist of about 500, 200, 100, 50, 30, 20, 10, 8, etc., the activation loop (e.g., amino acids 964–988, 950–988), etc. These polypeptides can be effective in eliciting an immune response to amino acid His968, and flanking regions thereof.

A PI3Kγ polypeptide mutein, comprising a sequence having at least 95% amino acid sequence identity to FIG. 3, and having a His968. Such a mutein can lack any of the mentioned activities of PI3K, but still retain its lipid kinase activity.

The present invention also relates to a method of modulating Ras activity in activating the PI3Kγ. Ras binding to PI3Kγ through its Ras binding domain ("RBD") leads to enzyme activation. The regions involved in the Ras interaction with PI3Kγ have been identified to include, e.g., a) specific regions of the N-terminal lobe of the catalytic region, such as kβ1–kβ2, kβ4–kβ5; kα6; b) RBD regions, such as Rα2 and Rβ3–Rβ4; and c) RBD residues, such as Lys234, Asp238, and Lys255. Modification of any these regions or specific residues can be effective in modulating Ras activity, e.g., inhibiting, blocking, decreasing, reducing, enhancing, increasing, etc., its activity. By the phrase, "Ras modulatory activity," it is meant any activity in which PI3K affects Ras, including binding to Ras, activating Ras, etc. Ras modulatory activity can be measured conventionally, e.g., as described in Bondeva et al., Science, 282:293–296, 1998.

The present invention also relates to PI3K polypeptides and muteins thereof which relate to the Ras modulatory activity. For instance, polypeptides involved in Ras modulatory and/or binding activity to PI3K, includes, e.g., kβ1–kβ2 (782–794), kβ4–kβ5 (816–825); kα6 (921–942); RBD regions, such as Rα2 (291–300) and Rβ3–Rβ4 (276–278), and fragments which comprise residues, such as Lys234, Asp238, and Lys255, e.g., Useful polypeptides include, e.g., polypeptides comprising, consisting of, consisting essentially, 782–816, 782–906, 795–816, 809–906, 817–906, and various combinations of any of the mentioned regions. A PI3K mutein can comprise 100% amino acid sequence identity with FIG. 3 at one or more of the above-mentioned domains, and less than 100% identity, such as 85%, 90%, 95%, 99%, or more, at any other regions of the PI3K. Since such mutein comprises the sequences that are used to interact with Ras, the mutein would possess Ras modulatory activity, but can lack other activities. A preferred Ras binding domain polypeptide consists essentially amino acid residues 220–311, having Lys234, Asp238, and Lys255, but less than 100% amino acid sequence identity at other positions, e.g., 70%, 75%, 80%, 85%, 90%, 95%, 99%, or more, at any other regions of the PI3K.

Antibodies, or other specific ligands, can be used to block Ras binding to PI3K, or the activation that results from such interaction. Regions a) and b) are involved in the intramolecular interaction of the N-terminal catalytic lobe with the RBD. Antibodies to any of such regions can block Ras interaction. Residues of RBD, such as Lys234, Asp238, and Lys255, form bonds with Ras (See, Table). Useful antibodies which block the Ras binding to PI3K, preferably include antibodies which are specific for a peptide comprising amino acids Lys234, Asp238, and, Lys255. In addition, antibodies to any of the above-mentioned regions which are involved with Ras modulatory can also be used.

The present invention also relates to methods of inhibiting the binding of PI3Kγ to cell membranes, comprising, e.g., modifying an amino acid a) the lining the crevice region between the N- and C-lobes (about residues 844–950, especially residues 844, 847, 947, 948, and 950 which form part of the phospholipid head-group pocket); b) the CBR regions (about residues 371–380, 401–407 and 434–459); or c) the region comprising the activation loop (about residues 964–989, especially 967). As already mentioned, "modifying" can mean replacing or chemically modifying amino acids in the mentioned domains, or contacting with ligands, such as antibodies, which recognize specifically the mentioned domains.

Additional surface residues of PI3K are, e.g., about 755–756, 807–808, 994–905, and 1077–1084. Thus, inhibiting or modifying any of these residues, as discussed above and below, are useful to prevent binding of PI3K to cell membranes.

Polypeptide fragments or muteins of PI3K which possess cell membrane binding activity can be used as modulators of the cell-membrane binding activity. For instance polypeptide fragments coding for regions a), b), and/or c), or parts thereof, can be administered in vivo or in vitro as antagonists to prevent an endogenous enzyme from targeting to cell membranes. Antibodies specific-for these regions can be used in the same way. A preferred polypeptide mutein has about 100% sequence identity with regions a), b), and/or c), and less than 100%, e.g., 99%, 95%, 90%, 85%, 80%, 70%, or more, sequence identity with the remaining regions of a PI3K shown in FIG. 3.

PI3K has a helical domain consisting of five A/B pairs of anti-parallel helices. Much of the B-surface is solvent exposed, providing a surface for interaction with other proteins, such as the p101 adaptor or Gβγ subunits. The present invention thus relates to modulating protein—protein interactions with PI3Kγ, comprising modifying the surfaces of the B-helices. The B-surfaces comprise, the exposed parts of B-helices, hB1 (570–577), hB1' (579–586), hB2 (601–613), hB2' (615–619), hB3 (638–650) hB4 (676–686), or hB5 (710–722). The modifying can comprise contacting said amino acid with an antibody specific-for hB1, hB1', hB2, hB2', hB3, hB4, or hB5, or by replacing, substituting, deleting, modifying, etc., an amino acid at such regions. A preferred polypeptide mutein or fragment (e.g., consisting essentially of 570–722) of a PI3Kγ comprises 100% sequence identity to hB1–hB5 of FIG. 3, and less than 100% sequence identity to the remaining sequence in FIG. 3, e.g., 50%, 60%, 70%, 75%, 80%, 85%, 90%, 95%, 99%, etc. Such mutein would retain the ability to interact with proteins.

Nucleic acids which code for any of the polypeptides, polypeptide fragments, and muteins thereof, can be prepared conventionally, using naturally-occurring or synthetic nucleotide sequences. See, e.g., Maniatis et al., Molecular Cloning, A Laboratory Mammal, Cold Spring Harbor Laboratory, Cold Spring Harbor, N.Y., 1989.

Antibodies, e.g., polyclonal, monoclonal, recombinant, chimeric, humanized, single-chain, Fab, etc., can be prepared according to any desired method. See, e.g., screening recombinant immunoglobulin libraries (e.g., Orlandi et al., Proc. Natl. Acad. Sci., 86:3833–3837, 1989; Huse et al., Science, 256:1275–1281, 1989); in vitro stimulation of lymphocyte populations (Winter and Milstein, Nature, 349: 293–299, 1991). For example, for the production of monoclonal antibodies, a polypeptide according to the present invention can be administered to mice, goats, or rabbits subcutaneously and/or intraperitoneally, with or without adjuvant, in an amount effective to elicit an immune response. The antibodies can be IgM, IgG, subtypes, IgG2a, IgG1, etc. Antibodies, and immune responses, can also be generated by administering naked DNA. See, e.g., U.S. Pat. Nos. 5,703,055; 5,589,466; 5,580,859.

Polypeptides for use in the induction of antibodies do not need to have biological activity; however, they must have immunogenic activity, either alone or in combination with a carrier. Peptides for use in the induction of specific-for antibodies may have an amino sequence consisting of at least five amino acids, preferably at least 10 amino acids. Short stretches of amino acids, e.g., five amino acids, can be fused with those of another protein such as keyhole limpet hemocyanin, or another useful carrier, and the chimeric molecule used for antibody production. Regions of PI3K useful in making antibodies are mentioned above and in the examples below.

The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241.

Antibodies and other ligands which bind PI3K can be used in various ways, including as therapeutic, diagnostic, and commercial research tools, e.g., to quantitate the levels of Pi3k polypeptide in animals, tissues, cells, etc., to identify the cellular localization and/or distribution of it, to purify it, or a polypeptide comprising a part of it, to modulate the function of it, in Western blots, ELIZA, immunoprecipitation, RIA, etc. The present invention relates to such assays, compositions and kits for performing them, etc.

In addition, ligands which bind to a PI3K according to the present invention, or a derivative thereof, can also be prepared, e.g., using synthetic peptide libraries or aptamers (e.g., Pitrung et al., U.S. Pat. No. 5,143,854; Geysen et al., J. Immunol. Methods, 102:259–274, 1987; Scott et al., Science, 249:386, 1990; Blackwell et al., Science, 250:1104, 1990; Tuerk et al., 1990, Science, 249: 505.).

A polypeptide of the present invention can be combined with one or more structural domains, functional domains, detectable domains, antigenic domains, and/or a desired polypeptide of interest, in an arrangement which does not occur in nature, i.e., not naturally-occurring. A polypeptide comprising such features is a chimeric or fusion polypeptide. Such a chimeric polypeptide can be prepared according to various methods, including, chemical, synthetic, quasi-synthetic, and/or recombinant methods. A chimeric nucleic acid coding for a chimeric polypeptide can contain the various domains or desired polypeptides in a continuous (e.g., with multiple N-terminal domains to stabilize or enhance activity) or interrupted open reading frame, e.g., containing introns, splice sites, enhancers, etc. The chimeric nucleic acid can be produced according to various methods. See, e.g., U.S. Pat. No. 5,439,819. A domain or desired polypeptide can possess any desired property, including, a biological function such as signaling, growth promoting, cellular targeting (e.g., signal sequence, targeting sequence, such as targeting to the endoplasmic reticulum or nucleus), etc., a structural function such as hydrophobic, hydrophilic, membrane-spanning, etc., receptor-ligand functions, and/or detectable functions, e.g., combined with enzyme, fluorescent polypeptide, green fluorescent protein, (Chalfie et al., Science, 263:802, 1994; Cheng et al., Nature Biotechnology, 14:606, 1996; Levy et al., Nature Biotechnology, 14:610, 1996), etc. In addition, a polypeptide, or a part of it, can be used as a selectable marker when introduced into a host cell. For example, a nucleic acid coding for an amino acid sequence according to the present invention can be fused in-frame to a desired coding sequence and act as a tag for purification, selection, or marking purposes. The region of fusion can encode a cleavage site to facilitate expression, isolation, purification, etc.

A polypeptide according to the present invention can be produced in an expression system, e.g., in vivo, in vitro, cell-free, recombinant, cell fusion, etc., according to the present invention. Modifications to the polypeptide imparted by such systems include glycosylation, amino acid substitution (e.g., by differing codon usage), polypeptide processing such as digestion, cleavage, endopeptidase or exopeptidase activity, attachment of chemical moieties, including lipids and phosphates, etc.

EXAMPLES

We have determined the structure of the catalytic subunit (residues 144–1102) of porcine PI3Kγ. This construct contains all of the homology regions found in class I PI3Ks (HR1, HR2, HR3 and HR4) and has a catalytic activity similar to the full length enzyme. The N-terminal region absent in our construct of PI3Kγ is important for interaction with the p101 adaptor (5), and the analogous region of PI3Kα interacts with the p85 adaptor. The enzyme has a modular structure consisting of four domains: a Ras-binding domain (RBD), a C2 domain, a helical domain and a catalytic domain (FIG. 1). The RBD, C2 and catalytic domains have folds similar to these modules in other proteins involved in signal transduction. The helical domain has a fold akin to HEAT-repeat containing structures involved in protein—protein interactions.

Figure 2:
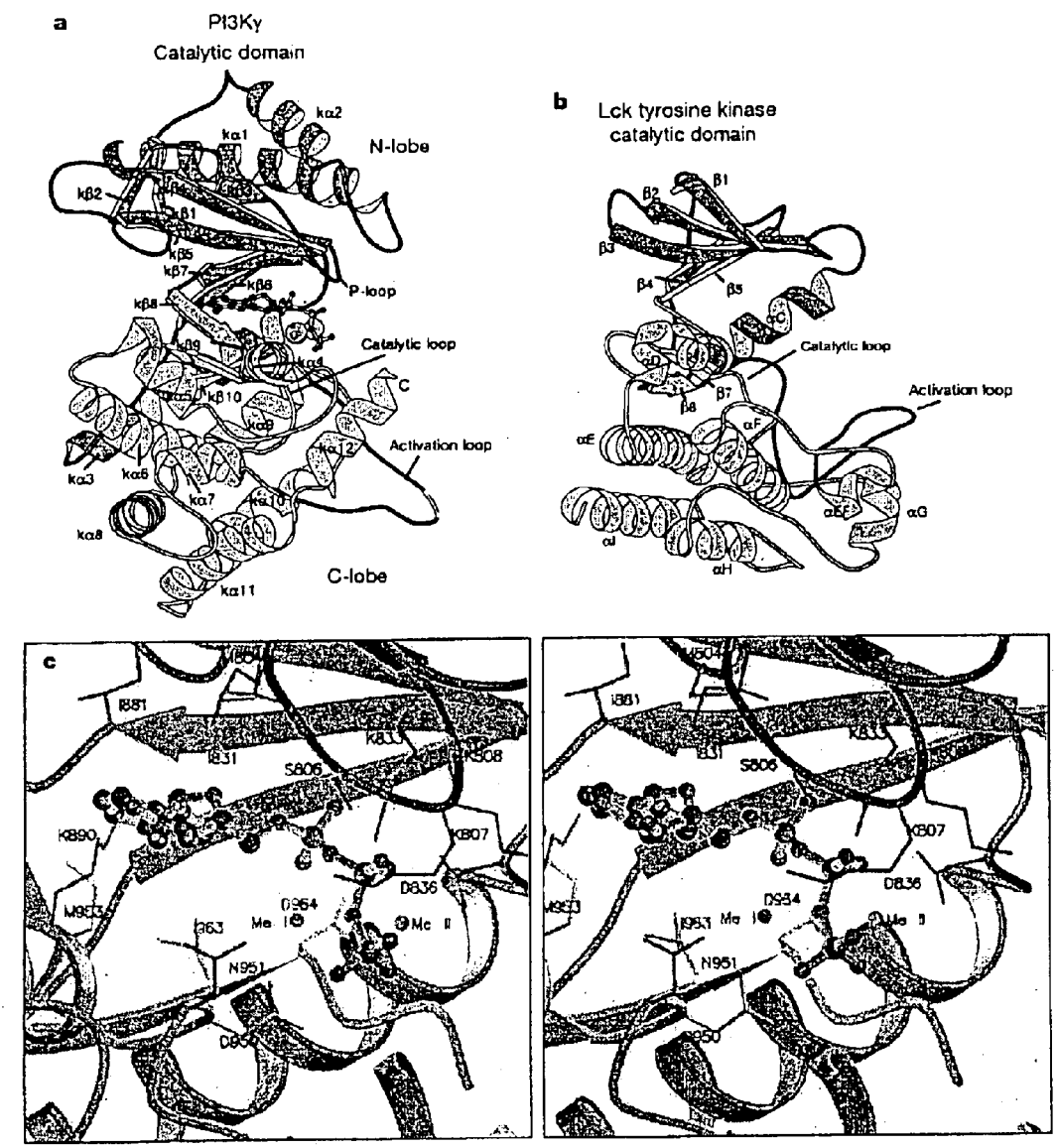
FIG. 2 shows a schematic representation of the catalytic domain of PI3K. (A) A ribbon diagram of the PI3K catalytic domain with bound ATP. The two disordered residues in the middle of the activation loop are represented by dotted lines. (B) The active conformation of the Src family protein kinase Lck (30) (PDB entry 3lck). (C) A stereo representation of PI3K active site with bound ATP and two $Lu^{3+}$ ions (labelled Me I and Me II).

The catalytic domain of the enzyme consists of a smaller N-terminal lobe (residues 726–883) and a larger C-terminal lobe (884–1092). The portion of the N-terminal lobe from kβ3 to kα3 and the first part of the C-terminal lobe (up to the end of kβ10) have a fold similar to protein kinases (reviewed in (6)), and this similarity extends to many of the details of the ATP binding site (FIG. 2). This region is among the most conserved regions of the PI3Ks (FIG. 3). The structural similarity of PI3K to protein kinases is consistent with finding that PI3Ks have a protein kinase activity in addition to their lipid kinase activities (7,8). The sequence alignment in FIG. 3 illustrates the regions of the enzyme that structurally superimpose with tyrosine protein kinase c-Src. The N-terminal lobe consists of a five-stranded antiparallel β-sheet flanked on one side by a helical hairpin (kα1–kα2) and a small two-stranded, β-sheet (β1–β2) and on the other side by the kα3 helix and the C-terminal lobe. Strands kβ3–kβ7 correspond to the five-stranded β-sheet found in the protein kinases. The kβ3–kβ4 loop corresponds to the protein kinase β1–β2 loop (also known as the glycine-rich or P-loop). This loop interacts closely with the phosphates of the bound ATP, but unlike the protein kinases, it contains no glycine. Instead, the side chain of Ser 806, a residue that is conserved in all PI3Ks, interacts with the β-phosphate (FIG. 2). Residue Lys 833 at the end of kβ5, corresponding to Lys 72 of c-AMP-dependent protein kinase, interacts with the α-phosphate of ATP. This residue is conserved in all PI3Ks and is covalently modified by Wortmannin (9). There are two metal binding sites (FIG. 2). Me I interacts with the conserved Asn 951 while Me II interacts with Asp 836 and Asp 964.

The link between the N- and C-terminal lobes is via a loop between strands kβ7 and kβ8. This loop forms the deepest wall of the ATP binding pocket and provides two hydrophobic contacts with the adenine moiety of the ATP. The C-terminal lobe forms a portion of the ATP binding site as well as the binding site for phospholipid substrates. The region between kα6 and kβ9 (residues 943–951) corresponds to the catalytic loop of the protein kinases. Mutations of residues in this loop analogous to Asp 946, Arg 947, Asp 950 and Asn 951 abolish kinase activity of PI3Ks (7,8).

Figure 4:
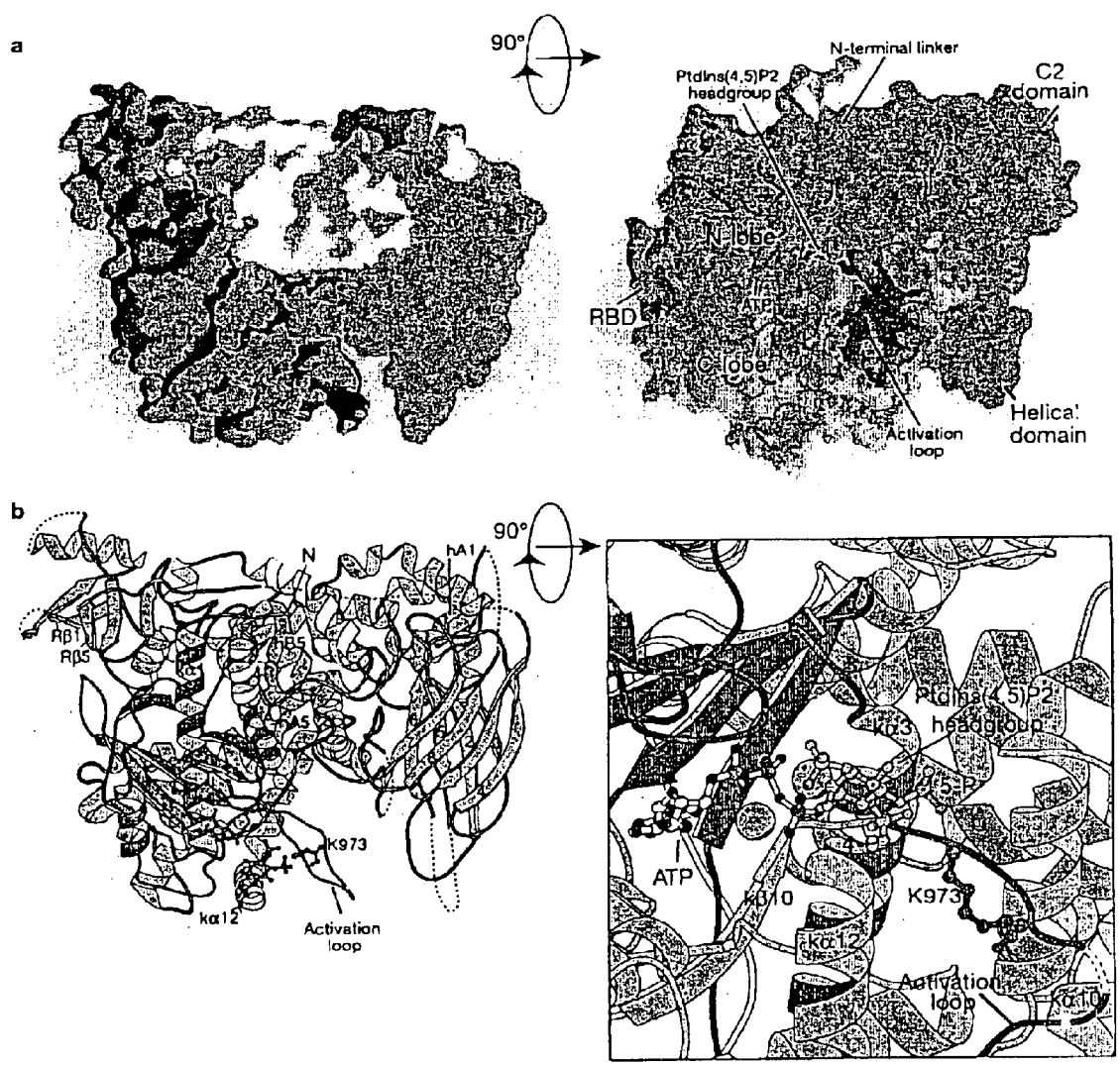
FIG. 4 is a model of phospholipid headgroup interactions with PI3K. (A) Two views of the solvent-accessible surface of the enzyme. The activation loop is coloured black. An inositol 1,4,5-trisphosphate (Ins$P_3$) molecule (white ball-and-stick) has been modelled in the active site with the 3-OH near the γ-phosphate of the bound ATP. (B) The same two views of the enzyme in ribbon representation with the activation loop and Ins$P_3$ cyan. The right portion of the panel has been expanded to illustrate some features of the putative headgroup interaction.

The C-terminal lobe contains a segment (964–988) analogous to the activation loop in the protein kinases; this loop is essential for the substrate specificity of the PI3Ks (10). In the ATP/Lu$^{3+}$ complex, much of this loop (968–982) is disordered. In the structure of an enzyme/chloramine T complex, all but two residues (Phe 975 and Leu 976) of this segment are visible, although high B-factors suggest that this loop is flexible. The activation loop is on the surface of the enzyme between the C-terminal helix kα12 on one side and kα10 on the other. We have attempted to soak phospholipid analogues into PI3Kγ crystals, but no substrate was evident in the electron density. Consequently, we have modelled phospholipid headgroup binding, but because conformational changes are likely to occur in the activation loop and possibly in the C-terminal helix upon substrate binding, the model is only approximate. In this model, the headgroup is positioned in a cavity lined by the C-terminal helix kα12, the activation loop and the catalytic loop (FIG. 4). This would place the 5-phosphate of a PtdIns(4,5)P$_2$ adjacent to Lys 973 and the 1-phosphate near Lys 807 and Lys 808. The involvement of Lys 973 as a ligand of the 5-phosphate might explain why this residue is not present in the class II PI3Ks which do not phosphorylate phosphoinositides with a 5-phosphate. The basic residues nearest the 4-phosphate are Arg 947 and Lys 973. The specificity of the class III PI3Ks for phosphatidylinositol might be explained by their shorter activation loop that might not leave sufficient space to accommodate a 4-phosphate at the bottom of the headgroup-binding pocket. PI3Kδ autophosphorylates in a region just beyond the C-terminal helix kα12 (11), resulting in enzyme inhibition probably by sterically preventing substrate binding. The proximity of the C-terminal segment to the substrate binding site is consistent with autophosphorylation of this region.

The mechanism originally proposed for the enzymatic activity of protein kinases involved participation of a residue acting as a general base to deprotonate the hydroxyl of the substrate generating a nucleophile that would attack the γ-phosphate of ATP. In cAMP-dependent protein kinase (cAPK), Asp 166 has been proposed to play the role of this general base. This residue corresponds to Asp 946 of the PI3Kγ 946-DRH-948 sequence that is conserved in all PI3Ks. However, in the structure of PI3Kγ, Asp 946 is not positioned so that it could have the role of a general base catalyst. The constellation of residues in the active site in the presence of ATP/metal suggests that Asp 946 may simply have a structural role in maintaining the integrity of the ATP-binding pocket. Therefore, either the enzyme has no general base catalyst, in which case the mechanism could be primarily dissociative, involving a metaphosphate transition state (12) or a different residue assumes this role in the PI3Ks. One candidate for the role of a general base may be His 948. Although the side-chain of His 948 is not near the γ-phosphate of ATP, a rotation around χ1 would place the side chain in a location such that it might interact with the 3-hydroxyl of the lipid headgroup.

PI3Ks have been identified as one of the effectors for Ras proteins (reviewed in (13)). Binding of PI3K to Ras is affected by mutations in both switch I and switch II regions of Ras (residues 30–38 and 60–76, respectively) (14,15). These two regions are known to change conformation upon GTP binding and serve as binding sites for a diverse array of downstream effectors. However, mutations in these switch regions have been identified that differentially affect binding of various effectors.

Figure 5:
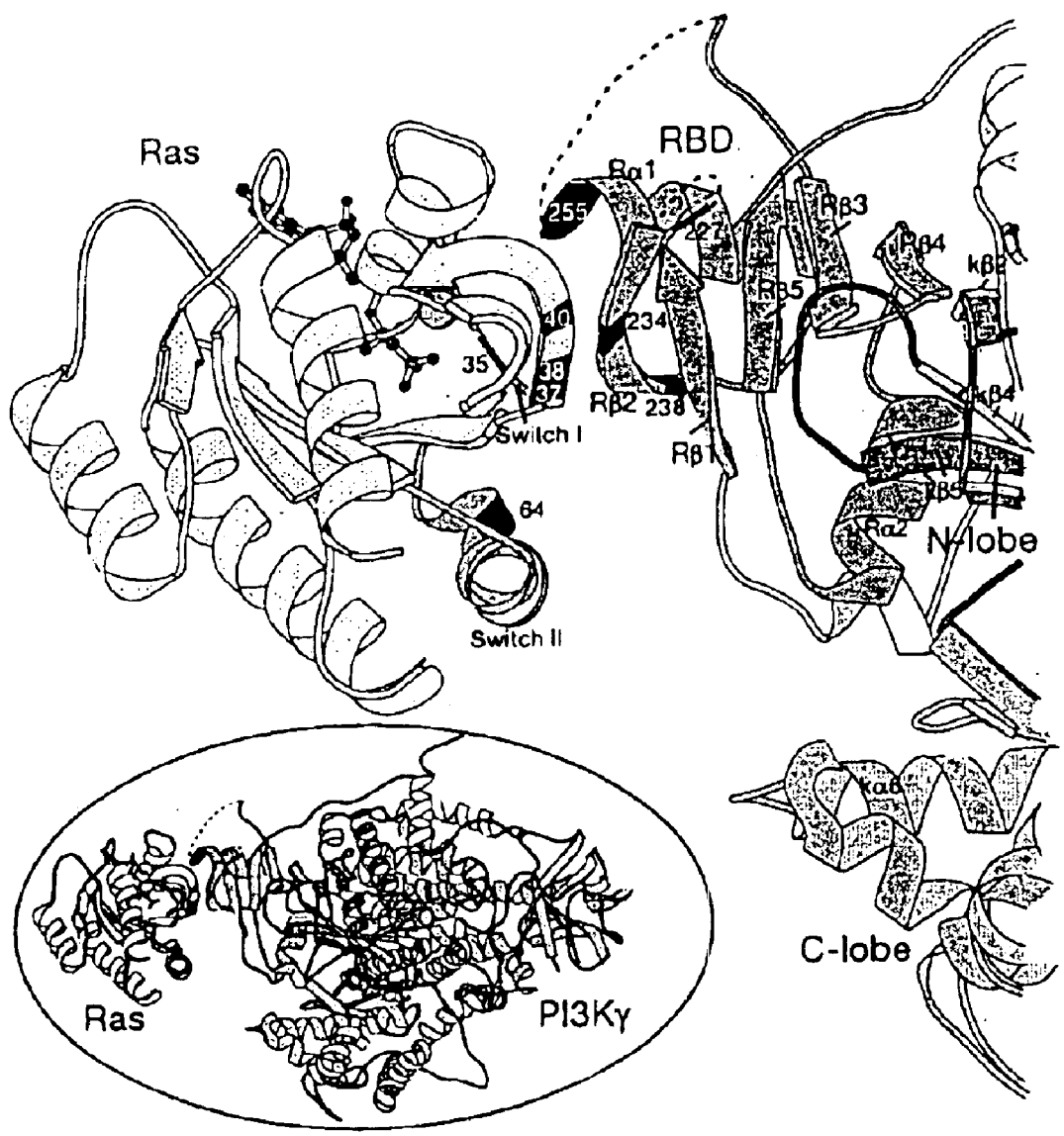
FIG. 5 shows a model of the Ras/PI3K interaction based on the structure of the RalGDS/Ras complex. The inset shows an overall view of Ras/PI3K interaction. Residues in Switch I and Switch II regions of Ras that influence effector binding are highlighted with stripes, while residues in the RBD of PI3K that are likely to be involved in Ras binding are shown as black stripes. The proximity of the RBD to the two lobes of the catalytic domain is also illustrated.

The structure reveals that the RBD of PI3Kγ (residues 220–311) has the same fold as the RBD of Raf (16) and RalGDS (17), two other well-characterised effectors of Ras (FIG. 5). The RBD of PI3K consists of a five-stranded mixed β-sheet (Rβ1–Rβ5) flanked by two α-helices (Rα1 and Rα2). Residues 228–230 (in the Rβ1/Rβ2 loop) and 257–265 (in the Rα1/Rβ3 loop) are disordered.

The crystal structure of Ras-related protein Rap1A in complex with the RBD of protein kinase c-Raf (16) and the structure of Ras in complex with the RBD of RalGDS (17), suggests a structural basis for effector specificity. For both of these complexes, the structure was determined with the isolated RBD, without the catalytic portions of the effector molecules. The PI3Kγ structure shows how the RBD interacts with the remainder of the enzyme. The RBD of PI3Kγ contacts the N-lobe and to a lesser degree the C-lobe of the catalytic domain. RBD residues in Rα2 and the Rβ3/Rβ4 loop interact with the catalytic domain, mainly with the kβ1/kβ2 and kβ4/kβ5 loops and helix kα6. The position of the RBD of PI3Kγ in relationship to the remainder of the enzyme allows for two possible mechanisms by which Ras binding might cause effector activation. One possibility is a recruitment mechanism whereby Ras increases PI3K activity by translocating the enzyme to the plasma membrane. A second possibility would be an allosteric mechanism in which Ras binding to the RBD causes a conformational change that would be propagated through the RBD/catalytic domain interface to affect substrate or co-factor binding.

By superimposing the RBDs of RalGDS and PI3Kγ, it is possible to construct a model of Ras interaction with PI3Kγ (FIG. 5). With this model, we can rationalise the differential effects of various switch I and switch II mutants on PI3K binding as opposed to other effectors. Mutations in Ras switch I residues T35S and D38E eliminate PI3K binding, but do not affect Raf binding (15). The E37G mutation abolishes binding to PI3K and Raf but not to RalGDS. The Y40C mutation does not affect PI3K binding, but abrogates Raf and RalGDS binding. In the switch II region, the Y64G mutation eliminates PI3K and neurofibromin binding but has no effect on Raf binding (14). In the model of the PI3K/Ras interaction, residues E37, D38, Y40 and Y64 would be at the PI3K/Ras interface. PI3K K234 would be in a position to form a salt bridge to E37 of Ras and K255 at the C-terminal end of Rα1 could form a salt link with D38 of Ras. K255 in PI3Kγ is probably analogous to K227 in PI3Kα. Mutation K227E blocks PI3Kα binding to Ras (15). Y40 interacts with K32 in RalGDS (numbering as in (17)). However, because of a very different orientation of the K32 equivalent in PI3Kγ (K234) this interaction may not be possible. This could account for the insensitivity of PI3K to the Y40C mutation. On the other hand, Y64 in switch II would be in a position to form a hydrogen bond with PI3K D238, but this residue has no specific interaction with RalGDS. This may explain the sensitivity of PI3K to the Ras Y64G mutation.

Figure 6:
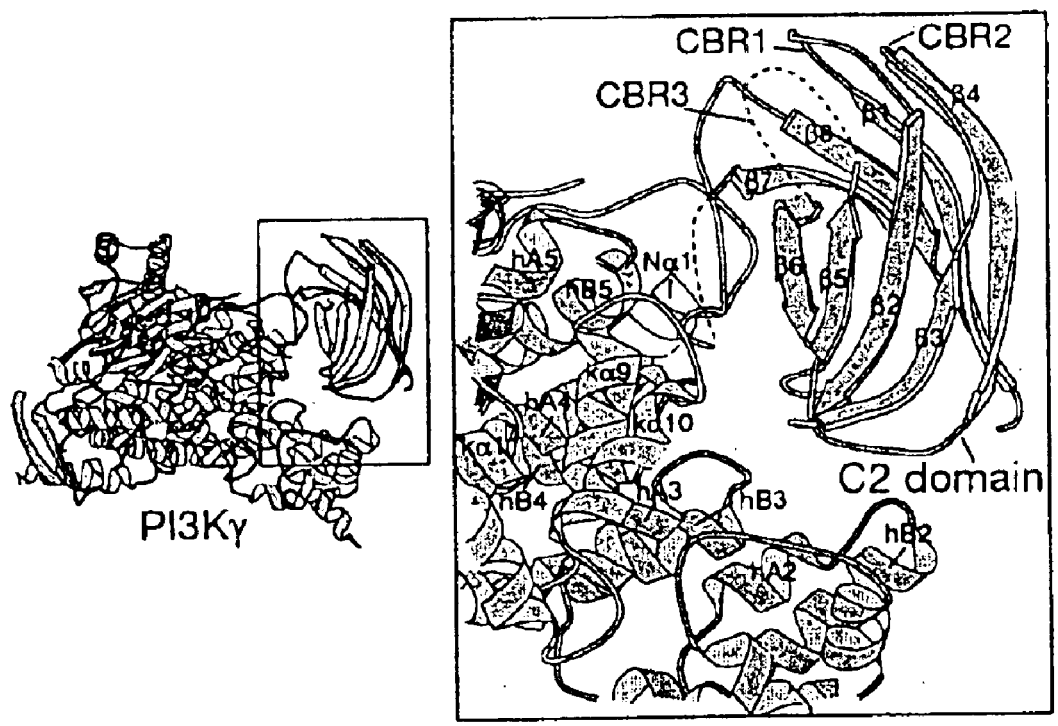
FIG. 6 is a ribbon diagram of the PI3KγC2 domain and the interactions it makes with the remainder of the enzyme. The elements of the helical and catalytic domains interacting with the C2 domain are shown. The inset shows the area selected for the detailed illustration.

The PI3Kγ C2 domain (residues 357–522) is an eight-stranded antiparallel β-sandwich consisting of two four-stranded β-sheets (FIG. 6). The fold of this domain is the same as the type II C2 domain found in PLCδ1[18]. The N-terminal regions of all three PI3K classes have C2 domains, while the class II enzymes have an additional C2 domain at the C-terminus (FIG. 1). The segments leading from the RBD into the C2 domain and from the C2 domain to the helical domain are not ordered.

C2 domains are often involved in $Ca^{2+}$-dependent or $Ca^{2+}$-independent phospholipid membrane binding using three loops known as CBRs located at one end of the domain. The CBRs for PI3Kγ are the loops connecting β1 with β2 (CBR1), β3 with β4 (CBR2), and β5 with β6 (CBR3). The CBR3 of PI3Kγ is quite long compared to other C2 domains and is disordered in our structure. The C2 domain interacts primarily with the helical domain, but it also interacts with the linker segment before the RBD and with the C-terminal lobe of the catalytic domain. The surface of the C2 domain contacting the rest of PI3Kγ is nearly identical to the surface of the PLCδ1 C2 domain that contacts the catalytic domain of PLCδ1.

PI3K can bind phospholipid membranes in the absence of other protein components, in a $Ca^{2+}$-independent manner and carry out processive catalysis at the membrane surface. By analogy with other enzymes such as protein kinase C and cytosolic phospholipase A2, it may be that the C2 domain of PI3K participates in membrane interaction. Consistent with this, we have found that the isolated C2 domain from PI3Kγ binds multilamellar phospholipid vesicles similarly to the full-length enzyme (data not shown). In PI3Kβ and PI3Kδ, CBR3 (residues 395–417 of PI3Kδ) is particularly rich in basic residues that may be important for membrane binding.

The structure of a type IIβ phosphatidylinositol phosphate kinase (PIPK) was recently reported (19). This dimeric enzyme, which phosphorylates phosphoinisitides at the 4-hydroxyl, consists of a single, catalytic domain. The dimer has an extensive flat, positively-charged surface that was proposed to be the membrane-binding interface of the enzyme. Although the N-lobe of PIPK is structurally related to the catalytic domain of PI3 Kγ, the location of the PI3Kγ C2 domain with respect to the catalytic domain would sterically preclude membrane interactions using the surface of PI3Kγ analogous to the putative PIPK membrane-binding surface. Given the location of the membrane-binding loops from the C2 domain and the cavity in the catalytic domain that must accommodate the $PtdIns(4,5)P_2$ headgroup, the membrane-binding surface of PI3Kγ would be such that the CBRs, the crevice between the N- and C-lobes of the catalytic domain and the tip of the activation loop would face the membrane interface (FIG. 4A, right panel would represent a view from the membrane surface).

Figure 7:
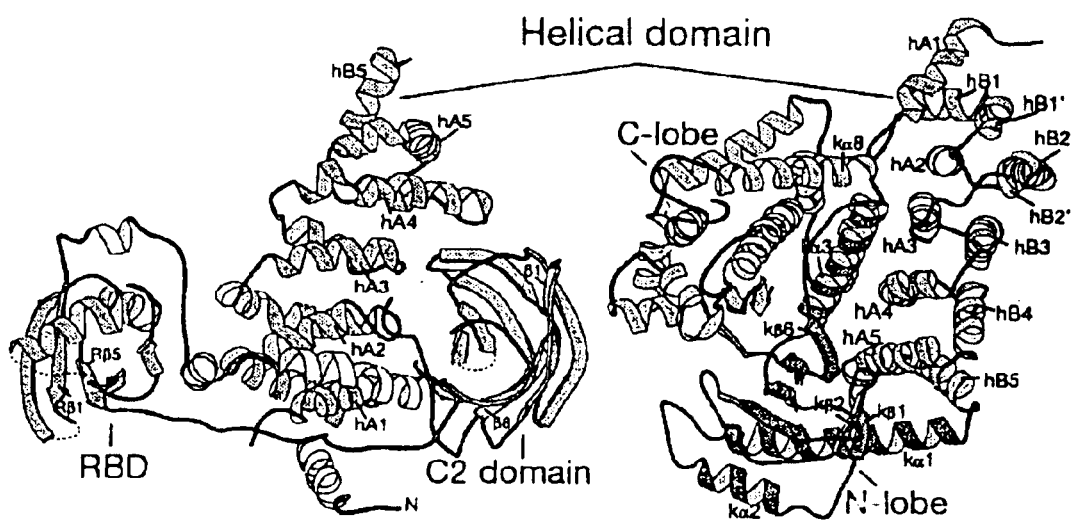
FIG. 7 is a schematic illustration of the helical domain. The A/B anti-parallel helical pairs characteristic of the HEAT motif topology consist of hA1/hB1, hA2/hB2, hA3/hB3, hA4/hB4 and hA5/hB5. The left half of the panel illustrates the interaction that the helical domain makes with the RBD and C2 domain (the remainder of the protein was removed for clarity). This interaction involves principally the A-helix surfaces. The interactions between the helical domain and the catalytic domain are shown on the right.

The helical domain of PI3K (residues 545–725) consists of five A/B pairs of anti-parallel helices (FIG. 7). The first two pairs have one kinked helix each, hB1/hB1' and hB2/hB2'. This region has been variously referred to as HR2, the PI3K accessory domain, and the PIK domain, but no clear function has been ascribed to this region. The paired arrangement of a series of helices connected into a right-handed super helix is reminiscent of the PR65/A regulatory subunit of protein phosphatase 2A (PP2A) (20). PR65/A is a member of a diverse group of proteins that contain between three and 25 tandem repeats of a short sequence that has been termed the HEAT motif. The HEAT motif consists of paired helices A and B arranged so that the A and B helices within a pair are anti-parallel and the A and B helices from one motif are parallel to the A and B helices of the next motif in the sequence. Although no HEAT sequence motif is apparent in the helical domain of PI3K, its structure is quite similar to that of PR65/A in terms of the arrangement of helices, the length of the A/B units, and the angle between the A/B pairs.

The function of HEAT repeats is to form protein/protein interactions. In the case of importin-β, the interactions that the protein makes with the small GTPase Ran involve primarily the surfaces of the B helices (21). For PR65/A, mutagenesis has implicated the loops connecting the A/B pairs as the region responsible for interaction with PP2A (20). In PI3Kγ, the helical domain is central to the inter-domain packing. The surface formed by the A helices interacts with the catalytic domain. The loops connecting A and B helices within a pair pack against the C2 domain while the loops between helical pairs pack against the RBD (FIG. 7). Much of the "B" surface is solvent-exposed and may interact with other proteins known to bind PI3Kγ such as the p101 adaptor or Gβγ subunits.

The helical domain is common to both PI3K and PI4K families and serves as a spine on which the other domains are fastened. One of the proteins in which the HEAT sequence motif was first noted is the target of rapamycin, TOR, a yeast homologue of human FRAP (reviewed in (22)). FRAP has a C-terminal domain with clear sequence homology to the catalytic domain of PI3Ks. The secondary structure prediction for the remainder of FRAP suggests that most of FRAP, apart from the catalytic domain, may consist of helical repeats folded into a right-handed superhelix as observed in the helical domain of PI3Kγ.

This first view of the structure of a PI3K provides a framework within which mutagenesis and detailed kinetic studies can be carried out to establish the enzymatic mechanism and the mode of activation by Ras and heterotrimeric G protein subunits.

Methods

Protein expression, purification and crystallisation. The cell-free extract of baculovirus-infected Sf9 cells expressing the His-tagged catalytic subunit of porcine PI3Kγ (residues 1–143 deleted) was used for protein purification using Talon resin, followed by thrombin cleavage, anion and cation exchange, and gel filtration chromatography. Crystals were grown by mixing 1 μl of PI3K (at 3.5 to 4.0 mg/ml, in a buffer containing 20 mM Tris-HCl pH7.2, 1% v/v ethylene glycol, 1% w/v betaine, 0.02% w/v CHAPS and 5 mM DTT) with 1 μl of a reservoir solution containing 150–200 mM $Li_2SO_4$, 100 mM Tris-HCl pH 7.25 and 14–15% PEG 4000.

Data collection and structure determination. Crystals have C2 symmetry with unit-cell dimensions of a=143.3 Å, b=67.6 Å, c=107.0 Å, β=95.9°, and contain one protein molecule in the asymmetric unit. Diffraction data were collected at ESRF beamlines ID2 and ID14-4. Data were collected at 100K after freezing crystals in a cryoprotectant consisting of 150–200 mM $Li_2SO_4$, 100 mM Tris-HCl pH 7.25, 12% glycerol and 20% PEG 4000. Data were processed using MOSFLM (23) and CCP4 programs (24). The structure was determined by multiple isomorphous replacement (MIR) methods. Heavy-atom positions were located using Solve (25) and refined with Sharp (26) (Table 1). A model was built into the electron density maps using the program O (27) and refined using CNS (28). The average B-factor for all atoms is 60 Å$^2$. The structure has no residues in disallowed regions of the Ramachandran plot.

The highest resolution data obtained were for the complex containing ATP and lutetium. Refinement of this complex resulted in a model with a free R-factor of 0.30 to a resolution of 2.2 Å. This complex has 854 residues visible in the electron density map. Comparison of crystals with and without ATP showed only minor differences in side-chain conformations in the active site residues. PI3Ks require a $Mg^{2+}$ or $Mn^{2+}$ cofactor for enzymatic activity. Complexes with $Lu^{3+}$, $Mg^{2+}$ or $Mn^{2+}$ show that each of the metals binds at the same two sites.

REFERENCES

1. Toker, A. & Cantley, L. C. Signalling through the lipid products of phosphoinositide-3-OH kinase. *Nature* 387, 673–676 (1997).
2. Domin, J. & Waterfield, M. D. Using structure to define the function of phosphoinositide 3-kinase family members. *FEBS Lett.* 410, 91–95 (1997).
3. Stoyanov, B. et al. Cloning and characterisation of a G protein-activated human phosphoinositide-3 kinase. *Science* 269, 690–693 (1995).
4. Stephens, L. R. et al. The Gβγ sensitivity of a PI3K is dependent upon a tightly associated adaptor, p101. *Cell* 89, 105–114 (1997).
5. Krugmann, S., Hawkins, P. T., Pryer, N. & Braselmann, S. Characterizing the interactions between the two subunits of the p101/p 110γ phosphoinositide 3-kinase and their role in the activation of this enzyme by Gβγ subunits. *J. Biol. Chem.* 274, 17152–17158 (1999).
6. Taylor, S. S. et al. Catalytic subunit of cyclic AMP-dependent protein kinase: structure and dynamics of the active site cleft. *Pharmacol. Ther.* 82, 133–141 (1999).
7. Dhand, R. et al. P13-kinase is a dual specificity enzyme-autoregulation by an intrinsic protein serine kinase activity. *EMBO J.* 13, 522–533 (1994).
8. Stack, J. H. & Emr, S. D. Vps34p required for yeast vacuolar protein sorting is a multiple specificity kinase that exhibits both protein kinase and phosphatidylinositol-specific PI-3-kinase activities. *J. Biol. Chem.* 269, 31552–31562 (1994).
9. Wymann, M. P. et al. Wortmannin inactivates phosphoinositide 3-kinase by covalent modification of Lys-802, a residue involved in the phosphate transfer reaction. *Mol. Cell. Biol.* 16, 1722–1733 (1996).
10. Bondeva, T. et al. Bifurcation of lipid and protein kinase signals of PI3Kγ to the protein kinases PKB and MAPK. *Science* 282, 293–296 (1998).
11. Vanhaesebroeck, B. et al. Autophosphorylation of p110δ phosphoinositide 3-kinase: a new paradigm for the regulation of lipid kinases in vitro and in vivo. EMBO J. 18, 1292–1302 (1999).
12. Kim, K. & Cole, P. A. Measurement of a Brønsted nucleophile coefficient and insights into the transition state for a protein tyrosine kinase. *J. Am. Chem. Soc.* 119, 11096–11097 (1997).
13. Marshall, C. J. Ras effectors. *Curr. Opin. Cell Biol.* 8, 197–204 (1996).
14. Moodie, S. A. et al. Different structural requirements within the switch II region of the Ras protein for interactions with specific downstream targets. *Oncogene* 11, 447–454 (1995).
15. Rodriguez-Viciana, P. et al. Role of phosphoinositide 3-OH kinase in cell transformation and control of the actin cytoskeleton by Ras. *Cell* 89, 457–467 (1997).
16. Nassar, M. et al. The 2.2 Å crystal structure of the Ras-binding domain of the serine/threonine kinase c-Raf1 in complex with Rap1A and a GTP analogue. *Nature* 375, 554–560 (1995).
17. Huang, L., Hofer, F., Martin, G. S. & Kim, S.-H. Structural basis for the interaction of Ras with RalGDS. *Nature Struct. Biol.* 5, 422–426 (1998).
18. Essen, L.-O., Perisic, O., Lynch, D. E., Katan, M. & Williams, R. L. A ternary metal binding site in the C2 domain of phosphoinositide-specific phospholipase C-δ1. *Biochemistry* 36, 2753–2762 (1997).
19. Rao, V. D., Misra, S., Boronenkov, I. V., Anderson, R. A. & Hurley, J. H. Structure of type IIβ, phosphatidylinositol phosphate kinase: a protein kinase fold flattened for interfacial phosphorylation. *Cell* 94, 829–839 (1998).
20. Groves, M. R., Hanlon, N., Turowski, P., Hemmings, B. A. & Barford, D. The structure of the protein phosphatase 2A PR65/A subunit reveals the conformation of its 15 tandemly repeated HEAT motifs. *Cell* 96, 99–110 (1999).
21. Vetter, I. R., Arndt, A., Kutay, U., Görlich, D. & Wittinghofer, A. Structural view of the Ran-importin β interaction at 2.3 Å resolution. *Cell* 97, 635–646 (1999).
22. Dennis, P. B., Fumagalli, S. & Thomas, G. Target of rapamycin (TOR): balancing the opposing forces of protein synthesis and degradation. *Curr. Opinion Genet. Develop.* 9, 49–54 (1999).
23. Leslie, A. G. W. Recent changes to the MOSFLM package for processing film and image plate data. in *Joint CCP4 and ESF-EACMB Newsletter on Protein Crystallography* Vol. 26, Daresbury Laboratory, Warrington, UK, 1992).
24. CCP4. Collaborative Computing Project Number 4: A suite of programs for protein crystallography. in *Acta Crystallogr.* D Vol. 50 760–763, 1994).
25. Terwilliger, T. C. & Berendzen, J. Automated structure solution for MIR and MAD. *Acta Crystallogr. D* 55, 849–861 (1999).
26. de La Fortelle, E. & Bricogne, G. Maximum-likelihood heavy-atom parameter refinement for multiple isomorphous replacement and multiwavelength anomalous diffraction methods. *Methods Enzymol.* 276, 472–494 (1997).
27. Jones, T. A., Zou, J.-Y., Cowan, S. W. & Kjeldgaard, M. Improved methods for building protein models in electron density maps and the location of errors in these models. *Acta Crystallogr. A* 47, 110–119 (1991).
28. Brunger, A. T. et al. Crystallography & NMR system: A new software suite for macromolecular structure determination. *Acta Crystallogr. D* 54, 905–921 (1998).
29. Nicholls, A., Sharp, K. A. & Honing, B. Protein folding and association: Insights from the interfacial and thermodynamic properties of hydrocarbons. *Proteins Struct. Funct. Genet.* 11, 281–296 (1991).
30. Yamaguchi, H. & Hendrickson, W. A. Structural basis for the activation of human lymphocyte kinase Lck tyrosine phosphorylation. *Nature* 384, 484–489 (1996).

The preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety. Walker et al., *Nature*, 402:313–320, is incorporated by reference in its entirety, including FIGS. 1–7.

TABLE 1

| Data set | Resolution (Å) | Observations/ unique reflections | Completeness (last shell) (%) | $R_{merge}$‡‡ | (I/σ) (last shell) | No. of sites | Phasing power‖ | $R_{ISO}$§§ |
|---|---|---|---|---|---|---|---|---|
| | | Data collection, structure determination and refinement statistics | | | | | | |
| Native*†† | 2.4 | 144,973/37,485 | 97.2 (90.6) | 8.5 | 16.0 (3.1) | — | — | — |
| LuCl$_3$-1†☆ | 2.2 | 191,292/49,599 | 95.5 (93.3) | 9.5 | 14.3 (1.1) | 7 | 1.7 | 0.23 |
| LuCl$_3$-2‡†† | 3.5 | 43,038/12,484 | 99.7 (98.2) | 8.5 | 11.3 (3.4) | 3 | 1.9 | 0.18 |
| Lanthanides§†† | 3.0 | 71,426/19,180 | 97.9 (97.1) | 4.5 | 15.6 (2.3) | 8 | 1.9 | 0.24 |
| ATM‖†† | 2.7 | 94,900/25,688 | 92.6 (60.2) | 4.8 | 17.0 (5.7) | 5 | 0.8 | 0.22 |
| Iodine¶†† | 2.6 | 102,511/28,856 | 93.2 (67.1) | 6.0 | 13.6 (1.4) | 3 | 0.1 | 0.21 |

| Data set | Resolution (Å) | Protein atoms | Waters | $R_{crystal}$¶¶ | $R_{free}$¶¶ (% data) | R m.s d from ideality ## Bonds | Angles | Dihedrals |
|---|---|---|---|---|---|---|---|---|
| Refinement statistics | | | | | | | | |
| LuCl$_3$-1 | 25.0–2.2 | 6,813 | 89 | 0.25 | 0.30 (5.4) | 0.013 Å | 1.7° | 23° |
| Iodine¶ | 25.0–2.6 | 6,954 | 14 | 0.26 | 0.33 (5.0) | 0.005 Å | 1.1° | 21° |
| Mn# | 25.0–2.6 | 6,837 | 26 | 0.26 | 0.32 (5.6) | 0.005 Å | 1.2° | 21° |
| Overall figure of merit 0.45 | | | | | | | | |

*The native crystal was soaked in 2.5 mM InsP$_3$, 1.0 mM ATP and 10 mM MgCl$_2$ for 1 h. Although this was the native crystal for heavy-atom phasing, the final high-resolution structure refinement used data from LuCl$_3$-1.
†LuCl$_3$-1 crystal was soaked in 20 mM LuCl$_3$ and 1.25 mM ATP for 1 h 40 min.
‡LuCl$_3$-2 crystal was soaked in 20 mM LuCl$_3$ and 1.3 mM ATP for 4 h.
§Lanthanides crystal was soaked for 4 h in a mixture of 3.3 mM each of GdCl$_3$, TbCl$_3$, HoCl$_3$, ErCl$_3$, TmCl$_3$, and LuCl$_3$ with 1.26 mM ATP and 1 mM EMTS.
‖ATM crystal was soaked for 22 h in 10 mM sodium aurothiomalate.
¶Iodine crystal was soaked for 75 min in 1 mM NaI$_3$ and 1 mM chloramine T. This crystal was originally prepared in an attempt to iodinate tyrosine residues as a heavy atom derivative, but no evidence of tyrosine iodination was seen in the resulting structure.
Mn crystal contained 1.4 mM ATP and 14 mM MnCl$_2$.
☆Data were collected at ESRF beamline ID2b.
††Data were collected at ESRF beamline ID14-4.
‡‡$R_{merge} = \Sigma_{h/d}\Sigma_i |I_i(hkl) - (I(hkl))|/\Sigma_{h/d}\Sigma I_i(hkl)$.
§§$R_{ISO} = \Sigma ||F_{deriv}| - |F_{native}||\Sigma |F_{native}|$.
‖The phasing power is defined as the ratio of the r.m.s. value of the heavy atom structure factor amplitudes and the r.m.s. value of the lack-of-closure error.
¶¶$R_{cryst}$ and $R_{free} = \Sigma |F_{abs} - F_{calc}|/\Sigma F_{abs}$; $R_{free}$ calculated with the percentage of the data shown in parentheses.
R.m.s. deviations for bond angles and lengths in regard to Engh and Huber parameters.

What is claimed is:

1. A crystal of a PI3Kγ catalytic domain, as set forth by residues 144–1102 of SEQ ID NO: 1, wherein the crystal has unit dimensions of a=143.3 Å, b=67.6 Å, c=107.0 Å, and β=95.9°.

* * * * *

SEQUENCE LISTING

<160> NUMBER OF SEQ ID NOS: 1

<210> SEQ ID NO 1
<211> LENGTH: 1102
<212> TYPE: PRT
<213> ORGANISM: Porcine PI3K

<400> SEQUENCE: 1

Met Glu Leu Glu Asn Tyr Glu Gln Pro Val Val Leu Arg Glu Asp Asn
1               5                   10                  15

Arg Arg Arg Arg Arg Arg Met Lys Pro Arg Ser Thr Ala Ala Ser Leu
                20                  25                  30

Ser Ser Met Glu Leu Ile Pro Ile Glu Phe Val Leu Pro Thr Ser Gln
            35                  40                  45

Arg Asn Thr Lys Thr Pro Glu Thr Ala Leu Leu His Val Ala Gly His
        50                  55                  60

Gly Asn Val Glu Gln Met Lys Ala Gln Val Trp Leu Arg Ala Leu Glu
65                  70                  75                  80

Thr Ser Val Ser Ala Asp Phe Tyr His Arg Leu Gly Pro Asp His Phe
                85                  90                  95

```
Leu Leu Leu Tyr Gln Lys Lys Gly Gln Trp Tyr Glu Ile Tyr Asp Lys
            100                 105                 110

Tyr Gln Val Val Gln Thr Leu Asp Cys Leu Arg Tyr Trp Lys Val Leu
        115                 120                 125

His Arg Ser Pro Gly Gln Ile His Val Val Gln Arg His Ala Pro Ser
    130                 135                 140

Glu Glu Thr Leu Ala Phe Gln Arg Gln Leu Asn Ala Leu Ile Gly Tyr
145                 150                 155                 160

Asp Val Thr Asp Val Ser Asn Val His Asp Asp Glu Leu Glu Phe Thr
                165                 170                 175

Arg Arg Arg Leu Val Thr Pro Arg Met Ala Glu Val Ala Gly Arg Asp
            180                 185                 190

Pro Lys Leu Tyr Ala Met His Pro Trp Val Thr Ser Lys Pro Leu Pro
        195                 200                 205

Glu Tyr Leu Leu Lys Lys Ile Thr Asn Asn Cys Val Phe Ile Val Ile
    210                 215                 220

His Arg Ser Thr Thr Ser Gln Thr Ile Lys Val Ser Ala Asp Asp Thr
225                 230                 235                 240

Pro Gly Thr Ile Leu Gln Ser Phe Phe Thr Lys Met Ala Lys Lys Lys
                245                 250                 255

Ser Leu Met Asp Ile Pro Glu Ser Gln Asn Glu Arg Asp Phe Val Leu
            260                 265                 270

Arg Val Cys Gly Arg Asp Glu Tyr Leu Val Gly Glu Thr Pro Ile Lys
        275                 280                 285

Asn Phe Gln Trp Val Arg Gln Cys Leu Lys Asn Gly Glu Glu Ile His
    290                 295                 300

Leu Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Thr Ala Asp Leu Thr Val Phe Val Glu
    370                 375                 380

Ala Asn Ile Gln Tyr Gly Gln Gln Val Leu Cys Gln Arg Arg Thr Ser
385                 390                 395                 400

Pro Lys Pro Phe Thr Glu Glu Val Leu Trp Asn Val Trp Leu Glu Phe
                405                 410                 415

Ser Ile Lys Ile Lys Asp Leu Pro Lys Gly Ala Leu Leu Asn Leu Gln
            420                 425                 430

Ile Tyr Cys Gly Lys Ala Pro Ala Leu Ser Gly Lys Thr Ser Ala Glu
        435                 440                 445

Met Pro Ser Pro Glu Ser Lys Gly Lys Ala Gln Leu Leu Tyr Tyr Val
    450                 455                 460

Asn Leu Leu Leu Ile Asp His Arg Phe Leu Leu Arg His Gly Glu Tyr
465                 470                 475                 480

Val Leu His Met Trp Gln Leu Ser Gly Lys Gly Glu Asp Gln Gly Ser
                485                 490                 495

Phe Asn Ala Asp Lys Leu Thr Ser Ala Thr Asn Pro Asp Lys Glu Asn
            500                 505                 510
```

-continued

```
Ser Met Ser Ile Ser Ile Leu Leu Asp Asn Tyr Cys His Pro Ile Ala
        515                 520                 525

Leu Pro Lys His Arg Pro Thr Pro Asp Pro Glu Gly Asp Arg Val Arg
        530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys Asp Pro Lys Ala Tyr Pro Lys Leu
                580                 585                 590

Phe Ser Ser Val Lys Trp Gly Gln Gln Glu Ile Val Ala Lys Thr Tyr
        595                 600                 605

Gln Leu Leu Ala Lys Arg Glu Val Trp Asp Gln Ser Ala Leu Asp Val
        610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
        660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
        690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
                725                 730                 735

Gln Val Ile Asp Met Leu Gln Lys Val Thr Ile Asp Ile Lys Ser Leu
        740                 745                 750

Ser Ala Glu Lys Tyr Asp Val Ser Ser Gln Val Ile Ser Gln Leu Lys
        755                 760                 765

Gln Lys Leu Glu Asn Leu Gln Asn Leu Asn Leu Pro Gln Ser Phe Arg
        770                 775                 780

Val Pro Tyr Asp Pro Gly Leu Lys Ala Gly Ala Leu Val Ile Glu Lys
785                 790                 795                 800

Cys Lys Val Met Ala Ser Lys Lys Pro Leu Trp Leu Glu Phe Lys
                805                 810                 815

Cys Ala Asp Pro Thr Ala Leu Ser Asn Glu Thr Ile Gly Ile Ile Phe
                820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
        850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
                885                 890                 895

Gly Asn Thr Gly Ala Phe Lys Asp Glu Val Leu Ser His Trp Leu Lys
                900                 905                 910

Glu Lys Cys Pro Ile Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
```

|   |   |   |   |   | 930 |   |   |   | 935 |   |   |   |   | 940 |   |
|---|---|---|---|---|---|---|---|---|---|---|---|---|---|---|---|
| Gly | Asp | Arg | His | Asn | Asp | Asn | Ile | Met | Ile | Ser | Glu | Thr | Gly | Asn | Leu |
| 945 | | | | | 950 | | | | | 955 | | | | | 960 |
| Phe | His | Ile | Asp | Phe | Gly | His | Ile | Leu | Gly | Asn | Tyr | Lys | Ser | Phe | Leu |
| | | | | 965 | | | | | 970 | | | | | 975 | |
| Gly | Ile | Asn | Lys | Glu | Arg | Val | Pro | Phe | Val | Leu | Thr | Pro | Asp | Phe | Leu |
| | | | 980 | | | | | 985 | | | | | 990 | | |
| Phe | Val | Met | Gly | Thr | Ser | Gly | Lys | Lys | Thr | Ser | Leu | His | Phe | Gln | Lys |
| | | 995 | | | | | 1000 | | | | | 1005 | | | |
| Phe | Gln | Asp | Val | Cys | Val | Lys | Ala | Tyr | Leu | Ala | Leu | Arg | His | His | |
| 1010 | | | | 1015 | | | | | 1020 | | | | | | |
| Thr | Asn | Leu | Leu | Ile | Ile | Leu | Phe | Ser | Met | Met | Leu | Met | Thr | Gly | |
| 1025 | | | | | 1030 | | | | | 1035 | | | | | |
| Met | Pro | Gln | Leu | Thr | Ser | Lys | Glu | Asp | Ile | Glu | Tyr | Ile | Arg | Asp | |
| 1040 | | | | | 1045 | | | | | 1050 | | | | | |
| Ala | Leu | Thr | Val | Gly | Lys | Ser | Glu | Glu | Asp | Ala | Lys | Lys | Tyr | Phe | |
| 1055 | | | | | 1060 | | | | | 1065 | | | | | |
| Leu | Asp | Gln | Ile | Glu | Val | Cys | Arg | Asp | Lys | Gly | Trp | Thr | Val | Gln | |
| 1070 | | | | | 1075 | | | | | 1080 | | | | | |
| Phe | Asn | Trp | Phe | Leu | His | Leu | Val | Leu | Gly | Ile | Lys | Gln | Gly | Glu | |
| 1085 | | | | | 1090 | | | | | 1095 | | | | | |
| Lys | His | Ser | Ala | | | | | | | | | | | | |
| 1100 | | | | | | | | | | | | | | | |